(12) United States Patent
Rytter et al.

(10) Patent No.: US 6,582,589 B2
(45) Date of Patent: Jun. 24, 2003

(54) PROCESS FOR THE CATALYTIC DEHYDROGENATION OF A LIGHT ALKANE

(75) Inventors: Erling Rytter, Trondheim (NO); Duncan Akporiaye, Oslo (NO); Unni Olsbye, Oslo (NO)

(73) Assignee: Oen Norske Stats Oljeselskap A.S., Stavanger (NO)

( * ) Notice: Subject to any disclaimer, the term of this patent is extended or adjusted under 35 U.S.C. 154(b) by 0 days.

(21) Appl. No.: 09/993,334

(22) Filed: Nov. 6, 2001

(65) Prior Publication Data

US 2002/0098976 A1 Jul. 25, 2002

Related U.S. Application Data

(63) Continuation of application No. 09/096,988, filed on Jun. 12, 1998, now Pat. No. 6,313,063, which is a continuation-in-part of application No. 08/569,185, filed as application No. PCT/NO94/00102 on Jun. 1, 1994, now Pat. No. 5,817,596.

(30) Foreign Application Priority Data

Jun. 14, 1993 (NO) ................................................ 932173

(51) Int. Cl.$^7$ .................. C10G 35/04; C10G 35/06; C07C 5/09; C07C 5/327; C07C 5/333
(52) U.S. Cl. .................. 208/134; 208/135; 208/137; 585/379; 585/616; 585/627; 585/654; 585/660
(58) Field of Search .................. 208/134, 135, 208/137; 585/379, 616, 627, 654, 660

(56) References Cited

U.S. PATENT DOCUMENTS 3,670,044 A    6/1972  Drehman et al. ......... 260/683.3
3,842,139 A   10/1974  Kehl et al. ................ 260/683.3
4,169,815 A   10/1979  Drehman ............... 252/466 PT
4,451,683 A    5/1984  Davies et al. ................ 570/224
4,788,371 A   11/1988  Imai et al. .................... 585/443
5,817,596 A  * 10/1998  Akporiaye et al. .......... 502/327
6,190,534 B1 *  2/2001  Bogdan ......................... 208/65
6,313,063 B1 * 11/2001  Rytter et al. ................. 502/327

FOREIGN PATENT DOCUMENTS

| EP | 0 251 351 B2 | 1/1988 |
| EP | 0 253 924 A1 | 1/1988 |
| EP | 0 323 115 B1 | 3/1993 |
| EP | 0 251 351 B1 | 8/1993 |
| GB | 2 225 731 A | 6/1990 |
| NO | B-179131 | 12/1994 |
| WO | WO 09/07980 | 7/1990 |
| WO | WO 94/29021 | 12/1994 |

* cited by examiner

Primary Examiner—Mark L. Bell
Assistant Examiner—Patricia L. Hailey
(74) Attorney, Agent, or Firm—Kirkpatrick & Lockhart LLP

(57) ABSTRACT

The present invention relates to a new catalyst support material comprising a mixed oxide consisting essentially of a divalent metal and a trivalent metal in a substantially homogeneous phase, the mixed oxide being a calcination product of a hydrotalcite-like phase calcinated at a temperature of about 700–1200° C., wherein the divalent metal/trivalent metal molar ratio is greater than or equal to 2. The invention also relates to a process of preparing the support. The invention further provides a catalyst for dehydrogenation which includes a transition metal selected from the first row of transition metals of the periodic table and/or a Group VIII metal impregnated on the new catalyst support material. The invention also provides a process for dehydrogenation of light alkanes using the catalyst.

12 Claims, 2 Drawing Sheets

PROCESS FOR THE CATALYTIC DEHYDROGENATION OF A LIGHT ALKANE

CROSS REFERENCE TO RELATED APPLICATIONS

This is a continuation of U.S. patent application Ser. No. 09/096,988, filed Jun. 12, 1998, now U.S. Pat. No. 6,313,063, which is a continuation in part of co-pending U.S. patent application Ser. No. 08/569,185, filed on Dec. 14, 1995, now U.S. Pat. No. 5,817,596, which is a 371 National Stage Application of international application No. PCT/NO94/00102, filed Jun. 1, 1994, and published as international publication No. WO 94/29021 on Dec. 22, 1994.

FIELD OF THE INVENTION

The present invention relates to the preparation of highly stable, high surface area catalyst carrier materials derived from hydrotalcite-type materials by calcination at an elevated temperature.

BACKGROUND OF THE INVENTION

The dehydrogenation of paraffins to olefins is of considerable commercial importance due to the need for olefins for the manufacture of products such as high octane gasolines, synthetic elastomers, detergents, plastics, ion exchange resins and pharmaceutical products. For a dehydrogenation process to be commercially useful, it must utilize catalysts exhibiting a high activity, a high rate of conversion, a high selectivity for the formation of olefins, and a high stability.

A large number of catalysts are previously known for the dehydrogenation of paraffins. These catalysts comprise a solid carrier material on an inorganic oxide base and various catalytic metals and promoter metals deposited on the carrier material or incorporated into the carrier material by other means. Carrier materials on an alumina base have been widely used in such dehydrogenation catalysts.

U.S. Pat. No. 4,788,371 discloses such catalyst and a process for the steam dehydrogenation of dehydrogenatable hydrocarbons with oxidative reheating. A dehydrogenatable $C_{2-30}$ hydrocarbon, steam and an oxygen-containing gas are contacted in a reaction zone with a catalyst comprising a Group VIII noble metal, one or more components selected from lithium, potassium, rubidium, cesium and francium, and a component selected from boron, gallium, indium, germanium, tin and lead, deposited on an inorganic oxide carrier material. The preferred carrier material is alumina having a surface area of 1–500 m$^2$/g, preferably 5–120 m$^2$/g. Alumina is employed as the catalyst carrier in all the working examples of the patent. A preferred catalyst according to said U.S. patent contains about 0.70 wt. % of platinum, about 0.50 wt. % of tin and about 3.86 wt. % of cesium, and has a surface area of about 85 m$^2$/g.

Mixtures of magnesium oxide MgO and alumina $Al_2O_3$ and mixed oxides of Mg and Al have also been utilized as catalysts, and as carrier materials for catalysts. International Patent Application No. PCT/JP89/00053 discloses an alkoxylation catalyst comprising a magnesium oxide that has been modified by adding thereto at least one trivalent metal ion, preferably selected from $Al^{3+}$ and $Ga^{3+}$. British Patent Application GB 2,225,731 discloses a catalyst for hydrotreatment, e.g. hydrodemetallization or hydrodesulphurization, comprising in a substantially homogenous phase magnesia and alumina wherein the molar ratio of Mg to Al is preferably from 3:1 to 10:1, together with a Group VI metal and/or at least one Group VIII metal.

Hydrotalcite is a layered mineral of formula: $Mg_6Al_2(OH)_{16}CO_3 \cdot 4H_2O$. Over the years, a large number of hydrotalcite-like compounds, of general formula: $[M(II)_{1-x}(III)_x(OH)_2]^{x+}(A^{n-}_{x/n}) \cdot mH_2O$, where A=anions, have been prepared. Cavani, F. et al., *Cat. Today*, vol.11, no.2, 173 (1991). These compounds are characterized by a sheet-like structure, in which the anions are located in the interlayer between two brucite-like sheets containing the metal ions. $M^{II}_1, M^{III}$ metal ions having an ionic radius which is not too different from $Mg^{2+}$ can form hydrotalcite-like compounds. Cavani, F. et al., supra.

Upon calcination at 400–700° C., a high surface area (typically 160–220 m$^2$/g) material with an XRD pattern typical for MgO is formed, without separation of the two metal ions into separate oxide phases. Schaper, H., et al., *Appl. Cat.*, vol. 54, 79 (1989). Upon calcination at even higher temperatures, the mixed oxide is gradually transformed into a spinel structure, i.e., $M^{II}M^{III}_2O_{4I}$ with a much lower surface area. McKenzie, A. L., et al., *J. Catal.*, vol. 138, 347 (1992); Bellotto, M., et al., *Phys. Chem.*, vol. 100, 8535 (1996). One major use for these materials is as support materials for catalysts, (see, Cavani, F. et al., supra) for instance for the catalytic dehydrogenation of lower alkanes. Akporiaye, D. et al., Norwegian Patent No. 179131 (1993). It has been reported that certain materials formed by calcination of a Mg—Al-containing hydrotalcite at 300–700° C. exhibit a high stability towards sintering in a humid atmosphere. See, Schaper, H., et al., *Appl. Cat.*, supra.; Schaper, H., European Patent No. 0 251 351 (1988).

SUMMARY OF THE INVENTION

The present invention provides a catalyst which has improved catalytic performance compared to prior art catalysts with regard to catalyst activity, and at the same time exhibits an increased catalyst life time by preventing irreversible deactivation like sintering of the support.

In one early embodiment of the invention described in co-pending U.S. patent application Ser. No. 08/569,185, it had been found that if a mixed oxide of Mg and Al is used in combination with a Group VIII noble metal and certain promoters of the kind disclosed in the above-mentioned U.S. Pat. No. 4,788,371, a catalyst can be obtained which exhibits improved activity and stability when used for dehydrogenating dehydrogenatable hydrocarbons.

The carrier for that embodiment of the catalyst may be prepared by adding a solution of sodium hydroxide and sodium carbonate to a solution of magnesium nitrate and aluminum nitrate according to the method described in *Journal of Catalysis*, vol. 94, pp.547–557, (1985), incorporated herein by reference. Instead of sodium hydroxide and sodium carbonate, potassium hydroxide and potassium carbonate can be used, see *Applied Catalysis*, vol. 55, pp. 79–90 (1989), incorporated herein by reference. A hydrotalcite-like compound $Mg_6Al_2(OH)_{16}CO_3 \cdot 4H_2O$ is formed by evaporation (drying) of the above-mentioned mixtures. The hydrotalcite is then calcinated at a temperature 500–800° C. to give Mg(Al)O. The molar ratio of Mg to Al typically ranges from 1:1 to 10:1, and the surface area is typically ranging from 100 to 300 m$^2$ per gram, preferably from 140 to 210 m$^2$ per gram, and the particle size can be in the range of 100 μm to 20 mm.

The calcination temperature for that embodiment of the catalyst was within the range of about 500 to about 800° C. A calcination temperature that had been shown to produce good results was about 700° C. In some of the examples set forth herein, this temperature was held for about 15 hours.

It has now been found, however, that the stability of the catalyst described herein could be further improved.

Thus, the present invention provides for a catalyst support material comprising a mixed oxide consisting essentially of a divalent metal and a trivalent metal in a substantially homogeneous phase, which is a calcination product of a hydrotalcite-like phase calcinated at a temperature of about 700–1200° C., wherein the divalent metal/trivalent metal molar ratio is equal to, or higher than 2.

Tests of the effect of the calcination temperature of hydrotalcite and hydrotalcite-like materials at different temperatures from 700° C. to 1200° C. were therefore investigated.

By performing these investigations, it has been surprisingly found that by raising the calcination temperature of the catalyst support precursor hydrotalcite to 700° C. to 1200° C., preferably to the range of 750 to 950° C., an improvement of the catalyst stability could be achieved with an acceptable reduction in the surface of the catalyst carrier compared to the gain in stability at use. In a further aspect, the present invention thus relates to a catalyst support material comprising a mixed oxide consisting essentially of Mg and Al in a substantially homogenous phase, which is a calcination product of a hydrotalcite phase, preferably calcinated at a temperature of 750 to 950° C., wherein the Mg/Al molar ratio is equal 2 or higher than 2. A most preferred range for the calcination has been found to be at 770 to 850° C., and within that range, the preferred temperature is at about 800° C.

Preferably the Mg/Al molar ratio is in the range of about 2.5 to 6.0, and most preferably, the Mg/Al molar ratio is in the range about 3 to about 5.

In another aspect of the present invention, a method for preparing said catalyst support material is provided wherein a solution comprising a divalent metal salt and trivalent metal salt is mixed with a basic aqueous solution, the reaction product recovered from said reaction mixture, said product being washed and dried, and the dried product is calcinated at a temperature ranging from about 700–1200° C. Calcination temperatures in the range of 750–950° C. have been found particularly suitable. More preferably the calcination takes place at a temperature ranging from about 770 to about 850° C. The best results have so far been achieved when the calcination was performed at about 800° C.

The calcination may be effected, for example, for about 1 to about 20 hours, and preferably the calcination is effected for about 2–15 hours.

The basic aqueous solution used in this process is preferably a composition of aqueous ammonium or alkali metal hydroxides and carbonates.

The preferred divalent metal therein is Mg and the preferred trivalent metal therein is Al.

The molar ratio of hydroxide to carbonate may, for example, be within the range of 1:1 to 3:1.

In another aspect, the present invention relates to a dehydrogenation catalyst comprising a transition metal, preferably a transition metal selected from the first row of transition metals of the Periodic Table and/or a Group VIII metal, impregnated on to the catalyst support described above.

Preferably the first row transition metal is Cr.

Preferably this catalyst comprises both a Group IVA metal and a Group VIII metal impregnated onto the catalyst support material mentioned above. Optionally a Group IA metal may be used together with the Group VIII metal and the Group IVA metal.

Preferably the Group VIII is Pt, the Group IV metal is Sn and the Group IA metal is Cs. Preferably the Group VIII metal catalyst is in the range of 0.05 to 5.0 percent by weight and the amount of the Group IVA metal is 0.05 to 7.0 percent by weight, optionally Group IA 0.05 to 5 percent by weight.

The present invention also relates to a process for the catalytic dehydrogenation of light alkanes wherein a stream of such light alkanes is passed through a layer of the catalytic active compositions described above in the presence or absence of steam.

Thus, according to one embodiment this process is performed in the presence of steam and in another embodiment, the process is performed in the absence of steam.

The present invention also relates to the use of the catalytic composition as described above for the dehydrogenation of light alkanes.

It had been found that the materials covered by the embodiment of the invention disclosed in co-pending United States patent application Ser. No. 08/569,185 and described in more detail herein, predominantly maintains the MgO structure, and also a high specific surface area and exhibited an improved stability towards sintering compared to the materials reported in Schaper, H., et al., *Appl. Cat.*, vol. 54, 79 (1989) and Schaper, H., European Patent No. 0 251 351 (1988), supra.

Preferably, the catalyst has been subjected to a pretreatment comprising a reduction, preferably in hydrogen, a subsequent oxidation, preferably in air optionally mixed with nitrogen, and finally a second reduction, preferably in hydrogen (ROR pretreatment; ROR=Reduction-Oxidation-Reduction).

The Group VIII noble metal is preferably selected from platinum and palladium, with platinum being the most preferred. The Group IVA metal is preferably selected from tin and germanium, with the most preferred metal being tin.

It has further been shown that the selectivity of the catalysts of the invention in a dehydrogenation process is further improved by including therein a Group IA alkali metal, preferably cesium or potassium, most preferably cesium.

It is remarkable that the new catalyst exhibits a very high activity in the dehydrogenation of hydrocarbons even with a low content of Group VIII noble metal of e.g. 0.2–0.4 wt. %.

The Group VIII metal, the Group IVA metal and the optional Group IA metal can be incorporated into the carrier by any of the methods known in the art. A preferred method consists in impregnating the oxide carrier with solutions or suspensions of decomposable compounds of the metals to be incorporated.

The catalyst and its preparation are described in more detail below with reference to embodiments wherein platinum, tin and optionally cesium are deposited on the carrier material, but the description is also valid for the deposition of other metals within the scope of the invention, with any adaptations that will be obvious to a person skilled in the art.

BRIEF DESCRIPTION OF THE DRAWINGS

The significance of the present invention can be better understood by reference to the drawings.

DETAILED DESCRIPTION OF THE INVENTION

Figure 1:
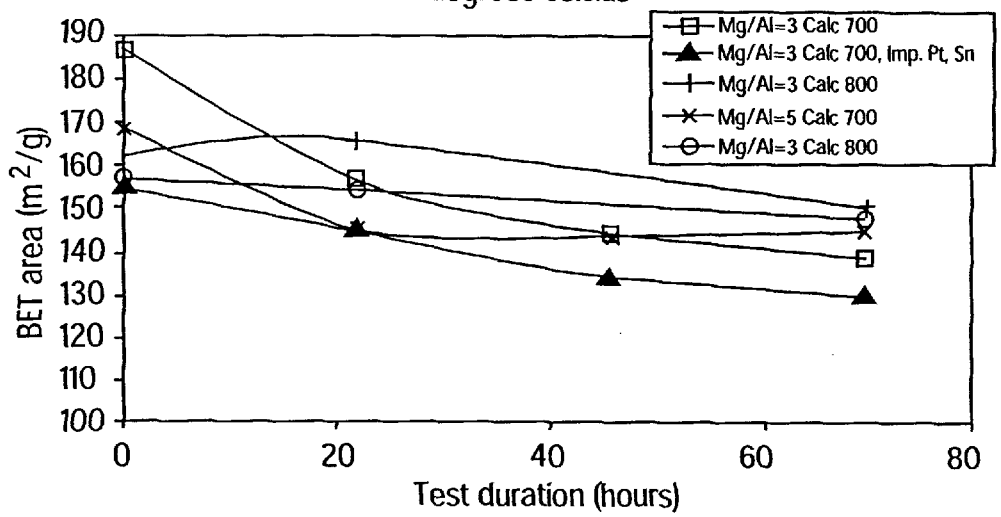
FIG. 1 shows steam stabilization tests at 650° C., materials prepared by Mg/Al ratio 3 and 5 and calcination temperature 700 and 800° C.

The present invention provides a dehydrogenation catalyst, a catalyst support and a method of preparing and for using the catalyst. In one embodiment of the invention, the catalyst includes a carrier, or catalyst support, and a Group VIII noble metal, a Group IVA metal, and otionally a Group IA alkali metal. The carrier may be a mixed oxide of magnesium and aluminum, Mg(Al)O, which is characterized by a magnesia structure wherein some of the magnesium atoms are replaced by aluminum atoms. The molar ratio of Mg to Al is typically ranging from 1:1 to 10:1, and the surface area is typically ranging from 100 to 300 m$^2$/g, preferably from 140 to 210 m$^2$/g. The particle size can be in the range of 100 μm to 20 mm.

The deposition of platinum and tin on the Mg(Al)O carrier material can advantageously be carried out in one step, e.g. by using tin chloride and hexachloroplatinic acid dissolved in ethanol. A method for depositing platinum and tin in a single step is described in J. Catalysis, vol. 128, 1 (1991). By carrying out a simultaneous deposition of platinum and tin on the Mg(Al)O material, the number of required calcination steps is reduced, which makes it easier to obtain a high surface area of the Mg(Al)O material. Other suitable impregnation procedures are described in the above-mentioned U.S. Pat. No. 4,788,371, in U.S. Pat. No. 4,962,265 and in EP 0,098,622, each incorporated herein by reference.

In cases where the catalyst contains cesium, a deposition of cesium can be effected in a separate step, after the deposition of tin and platinum and the subsequent calcination, using cesium nitrate dissolved in water. The impregnation with cesium nitrate can be carried out as described in U.S. Pat. No. 4,788,371.

The Reduction Oxidation Reduction (ROR) pretreatment of the catalyst is conveniently effected by carrying out a reduction of the catalyst in hydrogen, a subsequent oxidation in air optionally mixed with nitrogen, and finally a second reduction in hydrogen. The pretreatment can be carried out at temperatures in the range of 500° to 700° C. and by using space velocities (GHSV) for the treatment gases of 10 to 100,000 N ml g$^{-1}$ h$^{-1}$, preferably 100 to 5000 N ml g$^{-1}$ h$^{-1}$. The initial reduction of the catalyst with hydrogen is carried out for a period of 1 minute to 10 hours, usually for about 2 hours. The subsequent oxidation of the reduced catalyst in air optionally mixed with nitrogen is carried out for a period of 1 minute to 10 hours, usually for about 2 hours. The oxidation may advantageously be accomplished by first treating the catalyst for about 1 hour in a stream of nitrogen containing about 20% by volume of air, and then treating it for about 1 hour in pure air. The final reduction with hydrogen is carried out under similar conditions as the initial reduction.

Thus, the invention also relates to a process for preparing the above-described ROR pretreated catalyst. The process is characterized by the steps of incorporating a Group VIII noble metal, a Group IVA metal and optionally a Group IA alkali metal into a carrier consisting essentially of a mixed oxide of magnesium and aluminum Mg(Al)O, and subjecting the material thus obtained to ROR pretreatment comprising a reduction, preferably in hydrogen, a subsequent oxidation, preferably in air optionally mixed with nitrogen, and finally a second reduction, preferably in hydrogen.

The invention further provides a process for dehydrogenating dehydrogenatable $C_{2-30}$ hydrocarbons, preferably $C_{2-5}$ paraffins, comprising contacting the hydrocarbons, under suitable dehydrogenation conditions in one or more reaction zones, with a solid catalyst comprising a combination of a carrier, constituted essentially by a mixed oxide of magnesium and aluminum Mg(Al)O, a Group VIII noble metal, a Group IVA metal and optionally a Group IA alkali metal.

In accordance with usual practice in the dehydrogenation of hydrocarbons, the hydrocarbons are preferably contacted with the solid catalyst in a gaseous phase, mixed with usual additives such as steam, nitrogen and hydrogen. The feed mixture containing the hydrocarbons is preferably introduced into a reactor having one or more fixed catalyst beds, and the dehydrogenation is preferably carried out at a temperature ranging from 500° to 700° C., at a pressure ranging from 0.5 to 1.5 bars absolute, and using a space velocity (GHSV) ranging from 10 to 10.000 N ml g$^{-1}$ h$^{-1}$.

The new catalyst has also been shown to be very suitable in cases where the dehydrogenation of hydrocarbons is carried out in combination with admixing of oxygen and combustion of hydrogen, because the new catalyst also exhibits a selective catalytic effect on the oxidation of hydrogen to water.

It is well known in the art of dehydrogenating dehydrogenatable hydrocarbons that it is advantageous to oxidize with an oxygen-containing gas the hydrogen formed in the reaction. Because the dehydrogenation process is endothermic, oxidation of the formed hydrogen can be utilized to maintain the desired reaction temperature during the dehydrogenation. For such heating purpose it will often be advantageous even to add a supplementary amount of recirculated hydrogen to the reaction mixture. In addition to achieving a desired heat balance, the lowering of the hydrogen concentration in the reaction mixture resulting from the combustion will shift the equilibrium of the desired dehydrogenation reactions in the direction of higher yields of unsaturated hydrocarbons. Although it will be advantageous for that reason to achieve a high hydrogen conversion, it is important however to avoid excessive concurrent oxidation of hydrocarbons, which would reduce the total yield of the process. It is therefore important to achieve a maximum of selectivity of the oxidation of the hydrogen formed in the dehydrogenation process. It has been found that such selective oxidation is achieved with the new catalyst.

Thus, the invention also provides a process for dehydrogenating dehydrogenatable $C_{2-30}$ hydrocarbons, preferably $C_{2-5}$ paraffins, in combination with admixing of an oxygen-containing gas, preferably oxygen, and combustion of hydrogen, comprising contacting the hydrocarbons under suitable dehydrogenation conditions in one or more reaction zones, with a solid catalyst comprising a combination of a carrier, constituted essentially by a mixed oxide of magnesium and aluminum Mg(Al)O, a Group VIII noble metal, a Group IVA metal and optionally a Group IA alkali metal.

In accordance with usual practice in such dehydrogenation of hydrocarbons, the hydrocarbons are contacted with the solid catalyst in a gaseous phase, mixed with an oxygen-containing gas and with usual additives such as steam, any supplementary quantities of hydrogen, and nitrogen. The feed mixture containing the hydrocarbons is preferably introduced into a reactor having one or more fixed catalyst beds, with oxygen-containing gas being introduced and admixed with the feed stream even between the catalyst beds when more than one such bed is used. The dehydrogenation is preferably carried out at a temperature ranging from 400° to 700° C., at a pressure ranging from 0.5 to 3 bars absolute, and using a space velocity (GHSV) ranging from 10 to 10.000 N ml $g^{-1}$ $h^{-1}$.

In both of the two types of the dehydrogenation process the activity of the catalyst will decrease with time. When the activity has become undesirably low, the catalyst may be regenerated, e.g. in the same reactor. The regeneration can be carried out by burning off the coke that has been formed on the catalyst, with an oxygen-containing gas for a period of time ranging from 1 minute to 10 hours, preferably in a stream of air optionally mixed with nitrogen. The catalyst is then subjected to a reduction treatment for a period of 1 minute to 10 hours in a stream of hydrogen. Said treatments are suitably carried out at 300° to 700° C. using a space velocity (GHSV) for the treatment streams of 10 to 10,000 N ml $g^{-1}$ $h^{-1}$, preferably 100 to 5000 N ml $g^{-1}$ $h^{-1}$. If desired, a redispersion of the noble metal, e.g. platinum, in the catalyst can be effected using a chlorine-containing gas after the burning off of the coke but prior to the reduction treatment.

The regeneration of the catalyst restores to a substantial extent the original characteristics of the catalyst. The restoration of the activity and the selectivity of the catalyst will be more complete in the temperature range of 300° C. to 400° C. than at the higher temperatures. Admixing nitrogen with the air stream utilized for the oxidation also tends to improve the restoration of the properties of the catalyst.

Compared to the previously known dehydrogenation catalysts on an alumina base, the new catalyst exhibits improved activity and improved stability.

EXAMPLE 1

A Mg(Al)O material having an atomic ratio of Mg to Al of 2:1 to 3:1 was prepared according to the following procedure: An aqueous solution of 1.13 moles of NaOH and 0.045 mole of $Na_2CO_3$ was treated with a solution of 0.91 mole of $Mg(NO_3)_2 6H_2O$ and 0.09 mole of $Al(NO_3)_3 9H_2O$ at about 75° C. (pH=9.5). After filtration, washing and drying at about 100° C. for about 15 hours, a hydrotalcite $Mg_6Al_2(OH)_{16}CO_3 4H_2O$ was formed. The structure was confirmed by X-ray diffraction analysis. The material thus obtained was calcined at 700° C. for about 15 hours, whereby Mg(Al)O was formed. The structure was confirmed by X-ray diffraction analysis, and the surface area was measured to be 156 $m^2/g$.

EXAMPLE 2

A Mg(Al)O material having an atomic ratio of Mg to Al of 2:1 to 3:1 was prepared according to the following procedure: An aqueous solution of 1.13 moles of $NH_4OH$ and 0.045 mole of $(NH_4)_2CO_3$ was treated with a solution of 0.91 mole of $Mg(NO_3)_2 6H_2O$ and 0.09 mole of $Al(NO_3)_3 9H_2O$ at a temperature of about 75° C. (pH=9.5). After filtration, washing and drying at about 100° C. for about 15 hours, a hydrotalcite $Mg_6Al_2(OH)_{16}CO_3 4H_2O$ was formed. The material thus obtained was calcined at 700° C. for about 15 hours, whereby Mg(Al)O was formed. The structure was confirmed by X-ray diffraction analysis, and the surface area was measured to be 198 $m^2/g$.

EXAMPLE 3

A Mg(Al)O material having a particle size of 300–400 μm, prepared according to Example 1, was impregnated with a solution containing tin chloride and hexachloroplatinic acid and with a solution of cesium nitrate, according to the following procedure:

0.1150 g $SnCl_2 2H_2O$ and 0.0805 g $H_2PtCl_6 6H_2O$ were dissolved in 60 ml of ethanol and the mixture was added to 10.1 g of Mg(Al)O. After completion of the impregnation the material thus obtained was evaporated to dryness in a vacuum and was then dried at about 100° C. for about 15 hours, whereupon the dried material was calcined at 560° C. for about 3 hours in air supplied in an amount of 100 $cm^3/min$.

0.0711 g $CsNO_3$ dissolved in 25 ml of water was then added to the calcined material. Upon completion of the impregnation, the material thus obtained was dried at about 100° C. for about 15 hours. The dried material was calcined at 560° C. for about 3 hours in air supplied in an amount of 100 $cm^3/min$.

3 g of the calcined product were then reduced at 600° C. for 2 hours in a stream of $H_2$ supplied in an amount of 20 $cm^3/min$.

The reduced product was then oxidized at 600° C. for about 1 hour in a stream of $N_2$ containing 20% by volume of air, added in an amount of 50 $cm^3/min$, and for about 1 hour in pure air supplied in an amount of 50 $cm^3/min$. The oxidized product was then reduced in the same manner as before the oxidation.

A catalyst was obtained which had the following chemical composition:

0.3 wt. % Pt
0.6 wt. % Sn
0.5 wt. % Cs
98.6 wt. % Mg(Al)O.

The catalyst was tested for a dehydrogenation of propane in a microreactor equipped with a fixed catalyst bed, at the following conditions:

| | |
|---|---|
| Dehydrogenation temperature: | 600° C. |
| Dehydrogenation pressure: | 1 bar abs. |
| Space velocity (GHSV): | 2100 N ml $g^{-1}$ $h^{-1}$ |
| Amount of catalyst: | 3.0 g |
| Composition of the feed stream: | |
| Propane | 35 Nml/min |
| Hydrogen | 5 Nml/min |
| Nitrogen | 25 Nml/min |
| Steam | 41 Nml/min |

The results are given in Table 1.

EXAMPLE 4

Comparison Example

The procedure of Example 3 was repeated, with the following exception: After the first reduction of the calcined product with $H_2$, the oxidation in air-containing $N_2$ and the subsequent second reduction with $H_2$ were omitted.

The catalyst was used for a dehydrogenation of propane under the same conditions as in Example 3. The results obtained are given in Table 1.

EXAMPLE 5

The procedure of Example 3 was followed, including the post-treatment consisting in a reduction, a subsequent oxidation, and a second reduction (ROR pretreatment) of the calcined catalyst, but the impregnation with $CsNO_3$ for incorporation of cesium was omitted. The impregnation with a solution containing tin chloride and hexachloroplatinic acid was accomplished in the presence of quantities of tin chloride and hexachloroplatinic acid resulting in a catalyst having the chemical composition:

0.3 wt. % Pt
0.6 wt. % Sn
99.1 wt. % Mg(Al)O.

The catalyst was used for a dehydrogenation of propane under the same conditions as in Example 3. The results obtained are given in Table 1.

EXAMPLE 6

A Mg(Al)O material having a particle size of 300–400 μm, prepared according to Example 2, was impregnated with a solution containing tin chloride and hexachloroplatinic acid according to the following procedure:

0.1150 g $SnCl_2 2H_2O$ and 0.0805 g $H_2PtCl_6 6H_2O$ were dissolved in 60 ml of ethanol and the mixture was added to 10.1 g of Mg(Al)O. After completion of the impregnation the material thus obtained was evaporated to dryness in a vacuum and then dried at about 100° C. for about 15 hours, whereupon the dried material was calcined at 560° C. for about 3 hours in air supplied in an amount of 100 $cm^3$/min.

3 g of the calcined product were then reduced at 600° C. for 2 hours in a stream of $H_2$ supplied in an amount of 20 $cm^3$/min.

The reduced product was thereafter oxidized at 600° C. for about 1 hour in a stream of $N_2$ containing 20% by volume of air, supplied in an amount of 50 $cm^3$/min, and for about 1 hour in pure air supplied in an amount of 50 $cm^3$/min. The oxidized product was then reduced in the same manner as before the oxidation.

A catalyst was obtained which had the following chemical composition:

0.3 wt. % Pt
0.6 wt. % Sn
99.1 wt. % Mg(Al)O.

The catalyst was used for a dehydrogenation of propane under the same conditions as in Example 3. The results obtained are given in Table 1.

EXAMPLE 7

The procedure of Example 6 was followed, including the post-treatment consisting in a reduction, a subsequent oxidation, and a second reduction (ROR pretreatment) of the calcined catalyst, but the impregnation with a solution containing tin chloride and hexachloroplatinic acid was accomplished in the presence of quantities of tin chloride and hexachloroplatinum acid resulting in a catalyst having the chemical composition:

0.3 wt. % Pt
0.9 wt. % Sn
98.8 wt. % Mg(Al)O.

The catalyst was used in dehydrogenation of propane under the same conditions as in Example 3. The results obtained are given in Table 1.

EXAMPLE 8

The procedure of Example 6 was followed, including the post-treatment consisting in a reduction, a subsequent oxidation, and a second reduction (ROR pretreatment) of the calcined catalyst, but the impregnation with a solution containing tin chloride and hexachloroplatinic acid was accomplished in the presence of such quantities of tin chloride and hexachloroplatinum acid that a catalyst was obtained having the chemical composition:

0.3 wt. % Pt
1.2 wt. % Sn
98.5 wt. % Mg(Al)O.

The catalyst was used for a dehydrogenation of propane under the same conditions as in Example 3. The results obtained are given in Table 1.

EXAMPLE 9

Comparison Example

A known dehydrogenation catalyst was prepared according to the process disclosed in U.S. Pat. No. 4,788,371. 0.179 g of $SnCl_2 2H_2O$ dissolved in 14 ml of water was added to 18.8 g of θ-alumina having a particle size of 100 to 400 μm. After completion of the impregnation, the resulting material was dried at about 100° C. for about 6 hours. The dried material was calcined for about 3 hours at 600° C. in a stream of air supplied in an amount of 100 $cm^3$/min.

0.349 g of $H_2PtCl_6 6H_2O$ dissolved in 14 ml of water was added to the calcined material. After completion of the impregnation, the resulting material was dried at about 100° C. for about 15 hours. The dried material was calcined for a period of 3 hours at 570° C. in a stream of air containing 10% of steam and supplied in an amount of about 100 $cm^3$/min.

1.06 g of $CsNO_3$ dissolved in 14 ml of water were added to the calcined material. Upon completion of the impregnation, the resulting material was dried at about 100° C. for about 30 hours. The dried material was calcined for about 3 hours at 570° C. in an air stream supplied in an amount of about 100 $cm^3$/min.

3 g of the obtained catalyst were then reduced at 600° C. for about 2 hours in a stream of $H_2$ supplied in an amount of 20 $cm^3$/min.

A catalyst was obtained having the chemical composition:

0.7 wt. % Pt
0.5 wt. % Sn
3.9 wt. % Cs
94.9 wt. % θ-alumina.

The catalyst was used for a dehydrogenation of propane under the same conditions as in Example 3. The results obtained are given in Table 1.

EXAMPLE 10

Comparison Example

A catalyst was prepared according to Example 9, whereupon 3 g of the reduced catalyst were oxidized at 600° C. for about 1 hour in a stream of $N_2$ containing 20% by volume of air, supplied in an amount of 50 $cm^3$/min, and for about 1 hour in pure air supplied in an amount of 50 $cm^3$/min. The oxidized product was then reduced in the same manner as before the oxidation, i.e. at 600° C. for a period of 2 hours in a stream of $H_2$ supplied in an amount of 20 $cm^3$/min.

Thus, the post-treatment of the catalyst accomplished after the calcination corresponded to a ROR pretreatment as prescribed for the catalysts of the invention.

The catalyst was used for a dehydrogenation of propane under the same conditions as in Example 3. The results obtained are given in Table 1.

known catalyst for a dehydrogenation of propane accomplished in combination with combustion of hydrogen with an oxygen-containing gas. The combination of dehydroge-

TABLE 1

Dehydrogenation of propane to propene.

| Example | Carrier | Metal content (wt. %) | Conv. of propane 5 h (%) | Conv. of propane 25 h (%) | C-sel. to propene 5 h (%) | C-sel. to propene 25 h (%) | Yield propene[5] 25 h (%) |
|---|---|---|---|---|---|---|---|
| 3 | Mg(Al)O | 0.3 Pt<br>0.6 Sn<br>0.5 Cs | 52.8 | 45.6 | 97.5 | 97.8 | 44.6 |
| 4[1]<br>Comp. Cat. | Mg(Al)O | 0.3 Pt<br>0.6 Sn<br>0.5 Cs | 19.3 | 16.7 | 97.8 | 97.3 | 16.2 |
| 5 | Mg(Al)O | 0.3 Pt<br>0.6 Sn | 58.7 | 53.0 | 93.3 | 97.3 | 51.6 |
| 6[2] | Mg(Al)O | 0.3 Pt<br>0.6 Sn | 58.8 | 57.5 | 93.0 | 95.9 | 55.1 |
| 7[2] | Mg(Al)O | 0.3 Pt<br>0.9 Sn | 58.0 | 57.8 | 93.9 | 96.1 | 55.5 |
| 8[2] | Mg(Al)O | 0.3 Pt<br>1.2 Sn | 58.6 | 57.5 | 94.9 | 95.9 | 55.1 |
| 9[3]<br>Comp. Cat. | θ-Al$_2$O$_3$ | 0.7 Pt<br>0.5 Sn<br>3.9 Cs | 38.0 | 27.0 | 97.0 | 95.0 | 25.7 |
| 10[4]<br>Comp. Cat. | θ-Al$_2$O$_3$ | 0.7 Pt<br>0.5 Sn<br>3.9 Cs | 41.4 | 31.0 | 96.4 | 95.9 | 29.7 |

[1]Without ROR pretreatment.
[2]Mg(Al)O having a large surface area (198 m$^2$/g).
[3]A catalyst known from U.S. Pat. No. 4,788,371.
[4]A catalyst known from U.S. Pat. No. 4,788,371 but subjected to a ROR pretreatment.

[5]Yield of propene = $\dfrac{\text{Number of moles of C as C}_3\text{H}_6}{\text{Number of moles of C as C}_3\text{H}_8 + \text{Number of moles of C in products}}$ The results in Table 1 show that a ROR pretreated catalyst of the invention provides a large increase in the propane conversion compared to a similar catalyst not having been subjected to such pretreatment (Example 3 compared to Example 4). The selectivity for forming propene is retained at about the same level, whereby the total yield of propene is substantially increased.

The results in Table 1 also show that an increase in the surface area of the Mg(Al)O material from 156 m$^2$/g to 198 m$^2$/g results in a somewhat more stable catalyst and consequently in an increased yield of propene after 25 hours (Example 6 compared to Example 5).

An increase of the catalysts' content of Sn from 0.6 wt. % to 0.9 wt. % appears to result in a further increased yield of propene (Example 7 compared to Example 6).

The previously known catalyst of Example 9 gives a substantially lower yield of propene than the new catalysts (Examples 3, 5, 6, 7, 8). When the previously known catalyst of Example 9 is subjected to a complete ROR pretreatment as prescribed according to the invention (Example 10), the yield is improved even for said previously known catalyst. Nonetheless, the improving effect of the ROR pretreatment is not nearly as good for the known catalyst as for the new catalysts. Thus, the new catalysts also give a substantially better yield of propane than the ROR pretreated catalyst of Example 10.

EXAMPLE 11

The performance of one of the new catalysts of the invention was compared to the performance of a previously known catalyst for a dehydrogenation of propane accomplished in combination with combustion of hydrogen with an oxygen-containing gas. The combination of dehydrogenation and hydrogen combustion was carried out in a reactor comprising two catalyst zones and an intermediary oxygen admixing zone. In addition to oxygen being added to the feed to the first catalyst zone, oxygen was also introduced into said oxygen admixing zone between said two catalyst zones.

The new catalyst (I) consisted of 0.3 wt. % Pt and 1.2 wt. % Sn on Mg(Al)O and was a catalyst similar to the one of Example 8 above, except that it had been prepared with a particle size of 1–2 mm.

The known catalyst (II) was a catalyst according to U.S. Pat. No. 4,788,371, consisting of 0.65 wt. % Pt. 1.15 wt. % Sn and 2.18 wt. % Cs on θ-alumina. Catalyst (II) had been prepared according to said U.S. Pat. No. 4,788,371, as described in Example 9 above, except that similarly with the new catalyst (I) it had been prepared with a particle size of 1–2 mm.

The conditions employed in the combined dehydrogenation and hydrogen combustion, and the results obtained, are summarized in the following Table 2.

The results in Table 2 show that the new catalyst I and the known catalyst II, which are both described in Example 11, are both capable of achieving a selective oxidation of the hydrogen in the gas mixture.

The conversion of propane C$_3$H$_8$, and thus the yield of propene C$_3$H$_6$, is substantially higher for the new catalyst than for the known catalyst, viz. 57% versus 45% after 5 hours, and 55% versus 30% after 20 hours of operation, respectively. The higher propane yield was achieved in spite of the fact that the gas space velocity per gram of catalyst and per hour (GHSV) was higher for the new catalyst (2100 N ml g$^{-1}$ h$^{-1}$ versus 1400 N ml g$^{-1}$ h$^{-1}$ for the known catalyst), and in spite of the fact that the content of active noble metal (platinum) was substantially lower in the new catalyst (0.3 wt. % versus 0.65 wt. % in the known catalyst). The higher (GHSV) used with the new catalyst was due to the fact that this catalyst had a lower bulk weight than the known catalyst. As a consequence of the lower bulk weight of the new catalyst, the advantage resulting from its low content of platinum was even more important than suggested by the perceptual content alone. A low content of platinum in a commercial catalyst is important from an economical point of view.

The selectivity for oxidation of hydrogen to water is somewhat higher for the known catalyst than for the new catalyst, viz. 88% versus 80% after 5 hours, and 95% versus 87% after 20 hours of operation, respectively. This may be explained at least partly by the fact that the lower propane conversion achieved by the known catalyst resulted in the formation of lesser amounts of the desired dehydrogenated product, propane. Thus, with the known catalyst the oxidation of hydrogen to water was less burdened by competing oxidation of propene to carbon oxides.

Improvements in Stability

It has been found that improved stability is obtained using catalyst support materials comprised of a mixed oxide which consists essentially of a divalent metal and a trivalent metal in a substantially homogeneous phase. The mixed oxide is a calcination product of a hydrotalcite-like phase calcinated at a temperature of about 700–1200° C., wherein the divalent metal/trivalent metal molar ratio is greater than or equal to 2. The divalent/trivalent metals are preferably Mg and Al, with the Mg/Al molar ratio of the catalyst support material preferably being in the range of about 3 to about 5.

The catalyst is a dehydrogenation catalyst comprised of one or both of a transition metal selected from the first row of transition metals of the Periodic Table, or a Group VIII metal impregnated onto the catalyst support material. The first row transition metal is preferably Cr. The catalyst preferably has a Group IVA metal and optionally a Group 1A metal impregnated together with a Group VIII metal onto the catalyst support material described above. The Group VIII metal is preferably Pt. The Group IVA metal is preferably Sn, and the Group IA metal is preferably Cs. The amount of the Group VIII metal is preferably 0.05–5.0% by weight, the amount of the Group IVA metal is preferably 0.05–7.0% by weight, and the amount of the optional Group IV metal is preferably 0.05–5.0% by weight.

To prepare the catalyst support material, a solution comprising a divalent metal salt and a trivalent metal salt is mixed with a basic aqueous solution, preferably a composition of aqueous ammonium hydroxides and carbonates. The reaction product is recovered from the reaction mixture and product is washed and dried. The dried product is calcinated at a temperature ranging from 700–1200° C., preferably about 750–950° C., more preferably at about 770–850° C. and most preferably at about 800° C.

The steam testing discussed later in the following examples shows that materials calcinated at 800° C. after 72 hours have a higher specific surface area than those calcinated at 700° C. (See FIG. 1.) This involves a less frequent change of catalyst in the dehydrogenation process of light alkanes to alkenes. This less frequent changing of catalyst is of great importance when running a dehydrogenation reaction in industrial plants. This surprising improvement was not to be expected from the earlier catalyst calcined at 700° C. described above and in some examples set forth herein.

The following Examples are set forth to illustrate the invention disclosed herein. These examples should not, however, be construed as limiting the scope of the novel invention:

General

Calcination was performed under flowing air (100 ml/min). The sample (5–50 g) was heated with a heating rate of 3° C./min to the final calcination temperature. After completing the calcination, the sample was cooled with a cooling rate of approximately 2° C./min.

Specific surface area was measured using nitrogen by the BET method. The measurement accuracy was ±5%. Powder XRD (Siemens D-5000 diffractometer with Cu—K$_\alpha$radiation) was used to check crystallinity.

EXAMPLE 12

A Mg(Al)O material having an atomic ratio of Mg to Al of 3:1 was prepared according to the following procedure: An aqueous solution of 0.55 mole of NH$_4$OH and 0.045 mole of (NH$_4$)$_2$CO$_3$ was treated with a solution of 0.91 mole of Mg(NO$_3$)$_2$6H$_2$O and 0.09 mole of Al(NO$_3$)$_3$9H$_2$O at a temperature of about 60° C. (pH=9). After filtration, washing and drying at about 100° C. for about 15 hours, a hydrotalcite Mg$_6$Al$_2$(OH)$_{16}$CO$_3$4H$_2$O was formed. The material thus obtained was calcined at 700° C. for about 15 hours, whereby Mg(Al)O was formed. The structure was confirmed by X-ray diffraction analysis, and the surface area was measured to be 176 m$^2$/g.

EXAMPLE 13

A Mg(Al)O material having an atomic ratio of Mg to Al of 3:1 was prepared according to the following procedure: An aqueous solution of 1.13 moles of NaOH and 0.045 mole of Na$_2$CO$_3$ was treated with a solution of 0.91 mole of Mg(NO$_3$)$_2$6H$_2$O and 0.09 mole of Al(NO$_3$)$_3$9H$_2$O. After filtration, washing and drying at about 100° C. for about 15 hours, a hydrotalcite Mg$_6$Al$_2$(OH)$_{16}$CO$_3$4H$_2$O was formed. The structure was confirmed by X-ray diffraction analysis.

a) The material thus obtained was calcined at about 700° C. for about 15 hours, whereby Mg(Al)O was formed. The structure was confirmed by X-ray diffraction analysis, and the surface area was measured to be 187 m$^2$/g.

b) The material thus obtained was calcined at about 800° C. for about 15 hours, whereby Mg(Al)O was formed. The structure was confirmed by X-ray diffraction analysis, and the surface area was measured to be 162 m$^2$/g.

c) The material thus obtained was calcined at about 900° C. for about 15 hours, whereby Mg(Al)O was formed, together with traces of inverse MgAl$_2$O$_4$ spinel. The structure was confirmed by X-ray diffraction analysis, and the surface area was measured to be 110 m$^2$/g.

d) The material thus obtained was calcined at about 1000° C. for about 15 hours, whereby Mg(Al)O was formed, together with some inverse MgAl$_2$O$_4$ spinel. The structure was confirmed by X-ray diffraction analysis, and the surface area was measured to be 61 m$^2$/g.

EXAMPLE 14

A Mg(Al)O material having an atomic ratio of Mg to Al of 5:1 was prepared according to the following procedure: An aqueous solution of 1.13 moles of NaOH and 0.045 mole of Na$_2$CO$_3$ was treated with a solution of 0.91 mole of Mg(NO$_3$)$_2$6H$_2$O and 0.09 mole of Al(NO$_3$)$_3$9H$_2$O. After filtration, washing and drying at about 100° C. for about 15 hours, a hydrotalcite $Mg_6Al_2(OH)_{16}CO_3 4H_2O$ was formed. The structure was confirmed by X-ray diffraction analysis.

a) The material thus obtained was calcined at about 700° C. for about 15 hours, whereby Mg(Al)O was formed. The structure was confirmed by X-ray diffraction analysis, and the surface area was measured to be 169 m²/g.

b) The material thus obtained was calcined at about 800° C. for about 15 hours, whereby Mg(Al)O was formed. The structure was confirmed by X-ray diffraction analysis, and the surface area was measured to be 157 m²/g.

EXAMPLE 15

To investigate their steam stability, the support materials obtained as described in Examples 12, 13a) and 14a) were tested in a fluidized bed quartz apparatus. The steam stability test procedure was as follows:

The material was loaded into the reactor, which was then heated to 600° C. under a $N_2$ flow. When 600° C. was reached, steam was added to the feed. Such conditions (600° C., 50%$H_2O$/50%/$N_2$) were maintained for 22 hours. A sample of the material was then withdrawn from the reactor, and the temperature increased to 650° C. Such conditions (650° C., 50%$H_2O$/50%$N_2$) were maintained for 48 hours. New samples were withdrawn at 650° C. After completion of the test, the steam feed was turned off, and the reactor cooled to 25° C. under a $N_2$ flow. The remainder of the material was then collected. The sample materials were analyzed by BET and XRD.

Figure 3:
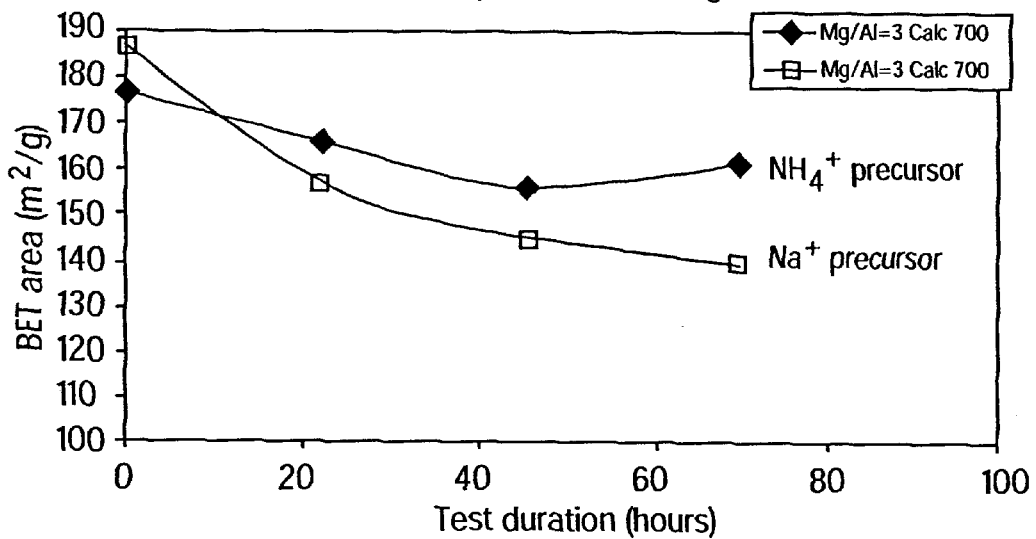
FIG. 3 shows steam stabilization tests at 650° C., materials prepared by Mg/Al=3 and calcination temperature 700° C. by using $NH_4^+$ or $Na^+$ salts in the precipitation of the materials.

The steam stability test results are shown in FIGS. 1 and 3. (Example 12 is only included in FIG. 3). The surface area in m²/g plotted along the vertical axis is expressed as a function of the duration of the steam stability test in hours (plotted along the horizontal axis).

EXAMPLE 16

To investigate the influence of calcination temperature on the materials' steam stability, the support materials obtained as described in Examples 13b) and 14b) were tested in a fluidized bed quartz apparatus, according to Example 15, but with a prolonged test duration at 650° C. (314 hours).

Figure 2:
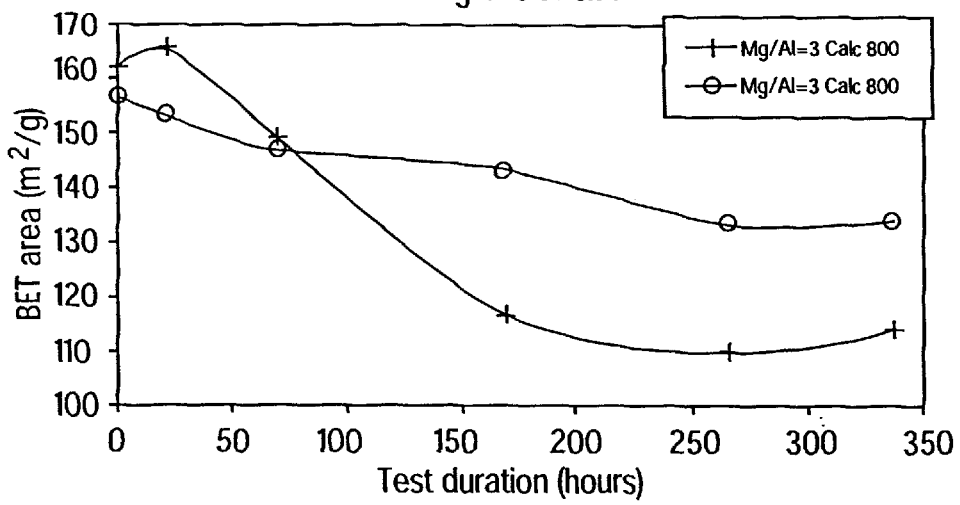
FIG. 2 shows steam stabilization tests at 650° C., materials prepared by Mg/Al ratio 3 and 5 and calcination temperature 800° C.

The results for the whole test (336 hours) are shown in FIG. 2. The test for the first 72 hours is shown in FIG. 1 together with the results from Example 15. The surface area in m²/g plotted along the vertical axis is expressed as a function of the duration of the steam stability test in hours (plotted along the horizontal axis).

EXAMPLE 17

Figure 4:
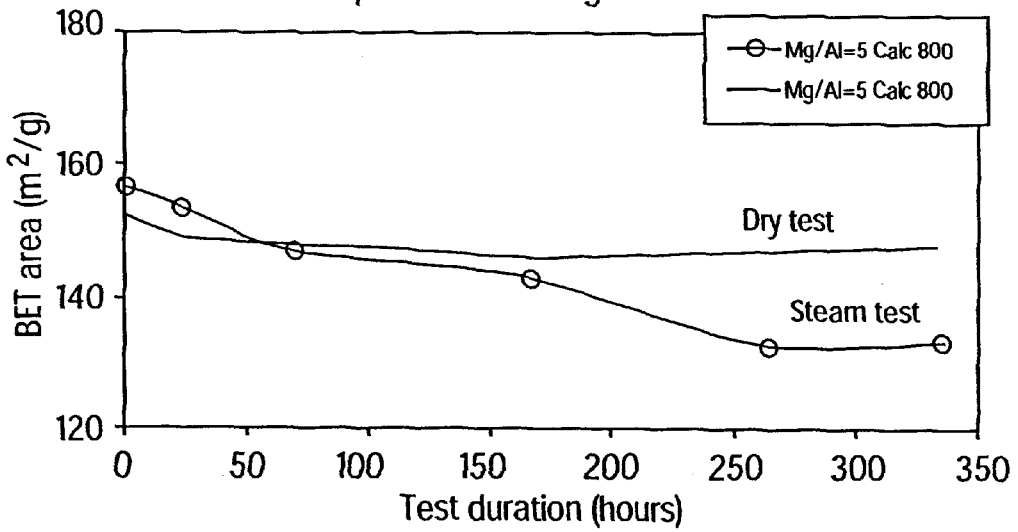
FIG. 4 shows steam stabilization test and thermion stabilization test at 650° C., materials prepared by Mg/Al=5 and calcination temperature 800° C.

To investigate its thermal stability, the support material obtained as described in Example 14b was tested as described in Example 16, except that 100% $N_2$ was used as feed gas during the whole test. The thermal stability test results are shown in FIG. 4.

EXAMPLE 18

A Mg(Al)O material having a particle size less than 100 μm, prepared according to any one of Example 12–14, was impregnated with a solution containing tin chloride and hexachloroplatinic acid according to the following procedure:

0.2304 g $SnCl_2 2H_2O$ and 0.0805 g $H_2PtCl_6 6H_2O$ were dissolved in 80 ml of ethanol and the mixture was added to 10.1 g of Mg(Al)O. After completion of the impregnation the material thus obtained was evaporated to dryness in a vacuum and was then dried at about 100° C. for about 15 hours, whereupon the dried material was calcined at 560° C. for about 3 hours in air supplied in an amount of 100 cm³/min.

EXAMPLE 19

To investigate its steam stability, a material prepared as described in Example 18, with Mg/Al ratio of 3, and which had been calcined at 700° C. prior to impregnation, was tested as described in Example 15. The steam stability test results are shown in FIG. 1.

EXAMPLE 20

To investigate its stability during catalytic testing, two materials prepared as described in Example 18, with a Mg/Al ratio of 3, and which had been calcined at 700 or 800° C. prior to impregnation, were pelletized by pressing, crushing and sieving to a pellet size of 0.7–1.0 mm, and tested as a catalyst for propane dehydrogenation. The tests were performed in a titanium laboratory scale fixed bed reactor with an inner diameter of 9 mm. A titanium tube with an outer diameter of 3 mm was located in the center of the reactor. The catalyst pellets were placed on a titanium sinter in the reactor. The reactor temperature was controlled by a thermocouple placed in the tube inside the reactor. The total pressure in the reactor was 1.1 bar. The catalysts (appx. 1 g) were tested under the following conditions: T=600–620° C., GHSV-600 h⁻¹ and $C_3H_6$:$H_2O$=1:2 (mole basis). The BET surface area measured before and after testing is shown in Table 3.

TABLE 3

| | Catalytic Testing | | |
|---|---|---|---|
| Calcination temperature | Test duration | BET surface area (m²/g), after: | |
| (° C.) | (h) | Pelletization | Testing |
| 700 | 380 | 124 | 112 |
| 800 | 380 | 131 | 121 |

The results presented in the Examples show that the initial surface area of the calcined materials decreases with increasing calcination temperature. The results presented in FIGS. 1 and 2 further show that the materials calcined at a higher temperature maintain a higher specific surface area during subsequent steam testing at 600–650° C. Indeed, for a steam test duration of more than 72 hours, the materials calcined at 800° C. have a higher specific surface area than those calcined at 700° C.

It is further observed that the initial specific surface area of the materials calcined at a certain temperature, decreases with an increasing Mg/Al ratio. During subsequent steam testing for 336 hours the material with a higher Mg/Al ratio maintain a higher specific surface area compared to the material with a lower Mg/Al ratio (FIG. 2). Indeed, after 50 hours of steam testing, the order of specific surface area is reversed, so that the materials with a higher Mg/Al ratio have a higher specific surface area than those with a lower Mg/Al ratio (FIG. 1).

Preparation of the material with $NH_4^+$ instead of $Na^+$ precursor led to a material with a slightly lower initial specific surface area but with a higher stability during steam testing (FIG. 3).

Impregnation of a calcined material with Pt and Sn led to a decrease in the initial specific surface area of that material. The subsequent decrease in specific surface area during steam testing was similar to that observed for the fresh material (FIG. 1).

Pelletization of the impregnated materials led to a decrease in their specific surface area (Table 3). Subsequent testing of the material as a propane dehydrogenation catalyst showed that the excellent surface area stability observed for these materials during steam testing, is also valid under catalytic test conditions. Even here, an improved stability was indicated for the material calcined at 800° C.

Finally, it is observed that the presence of steam is an important factor for the thermal stability of the materials covered by this invention: When no steam was added to the feed the specific surface area of a Mg/Al=5 material calcined at 800° C. was stable throughout a 334 hours test at 600–650° C. (FIG. 4).

This means that to prevent sintering of the catalyst support during the dehydrogenation of alkanes, the dehydrogenation can advantageously be performed without steam.

What is claimed is:

1. A process for the catalytic dehydrogenation of a light alkane, wherein a stream of a light alkane is passed through a layer of the catalyst, the catalyst comprising platinum and tin impregnated onto a catalyst support material comprising a mixed oxide consisting essentially of an oxide of a divalent metal and a trivalent metal in a substantially homogeneous phase, which mixed oxide is a calcination product of a hydrotalcite-like phase calcinated at a temperature of about 770° C. to about 1200° C., wherein the divalent metal to trivalent metal molar ratio is greater than or equal to 2, and wherein the platinum and tin contents of said hydrogenation catalyst range from 0.05% to 5% by weight and 0.05% to 7% by weight, respectively.

2. The process of claim 1 wherein said catalytic dehydrogenation is performed in the presence of steam.

3. The process of claim 1 wherein said catalytic dehydrogenation is performed in the absence of steam.

4. The process of claim 1 wherein said light alkane is a $C_{2-5}$ alkane.

5. The process of claim 1 wherein said catalytic dehydrogenation is carried out at a temperature ranging from 400° C. to 700° C.

6. The process of claim 1 wherein the divalent metal is Mg and the trivalent metal is Al.

7. The process of claim 6 wherein the molar ratio of Mg to Al is in the range of about 2.5 to about 6.0.

8. The process of claim 7 wherein the molar ratio of Mg to Al is in the range of about 3 to about 5.

9. The process of claim 1 wherein the hydrotalcite-like phase is calcinated at a temperature of about 770° C. to about 850° C.

10. The process of claim 1 wherein the hydrotalcite-like phase has been calcinated at a temperature of about 800° C.

11. The process of claim 1 wherein the hydrotalcite-like phase has been calcinated at a temperature of about 770° C. to about 1200° C. for about 1 to about 20 hours.

12. The process of claim 1 wherein the catalyst has been subjected to a first reduction, an oxidation, and a second reduction.

* * * * *